United States Patent [19]
Igaue et al.

[11] Patent Number: 4,822,435
[45] Date of Patent: Apr. 18, 1989

[54] METHOD FOR MAKING WEARABLE ARTICLES

[75] Inventors: Takamitsu Igaue; Hiroyuki Tanji, both of Kawanoe, Japan

[73] Assignee: Uni-Charm Corporation, Ehime, Japan

[21] Appl. No.: 112,361

[22] Filed: Oct. 26, 1987

[30] Foreign Application Priority Data

Oct. 27, 1986 [JP] Japan .................................. 61-254892
Jan. 28, 1987 [JP] Japan .................................. 62-19338

[51] Int. Cl.$^4$ ............................................ B32B 31/08
[52] U.S. Cl. .................... 156/164; 156/201; 156/202; 156/204; 604/358; 604/385.2
[58] Field of Search ............... 156/164, 182, 197, 201, 156/202, 216, 229, 554, 163, 204; 604/358, 380, 385.1, 385.2, 378, 394; 428/152, 77, 121, 122-123

[56] References Cited
U.S. PATENT DOCUMENTS 4,430,086  2/1984  Repke .................................. 604/385.2
4,695,278  9/1987  Lawson .............................. 604/385.1
4,738,677  4/1988  Foreman .......................... 604/385.1

Primary Examiner—David Simmons
Assistant Examiner—David Herb
Attorney, Agent, or Firm—Fred Philpitt

[57] ABSTRACT

Here is disclosed a method for making wearable articles such as disposable diapers, disposable diaper covers or the like, more particularly, a method for formation of side flaps provided with elastic members for a desired fitness around the wearer's legs. This method comprises steps of forming a main body of the article having first side flaps extending outwards from opposite sides thereof, forming second side flaps separately of the main body, providing the second side flaps along the respective one side edges with elastic members, and joining the second side flaps along the respective other side edges and longitudinally opposite ends thereof to the top surfaces of the respective first side flaps so that the respective one side edges of the second side flaps along which the respective elastic members are disposed are directed outwards.

3 Claims, 6 Drawing Sheets

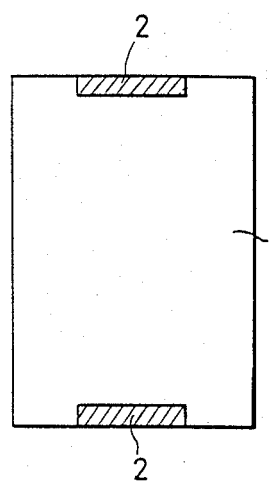
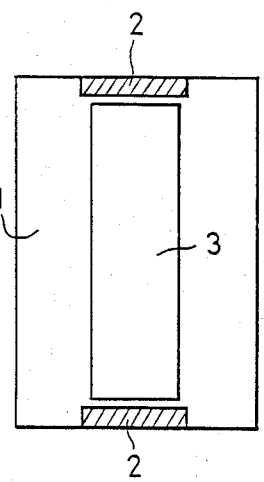
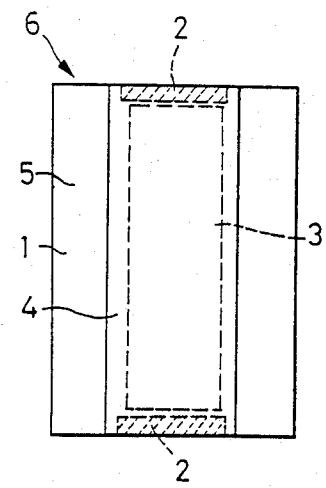
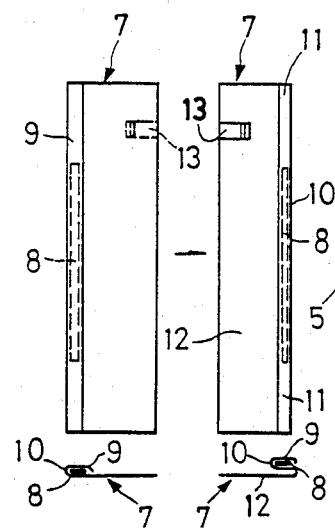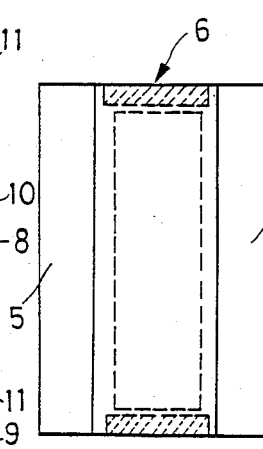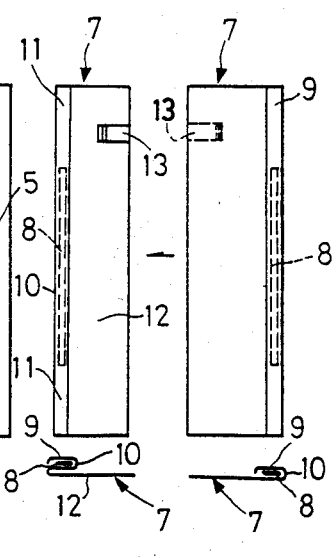

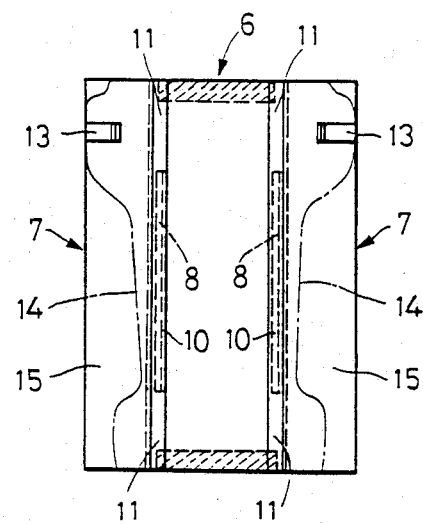
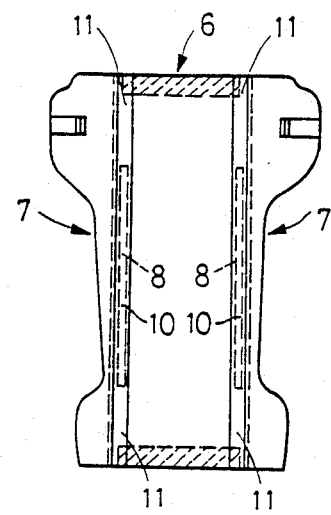
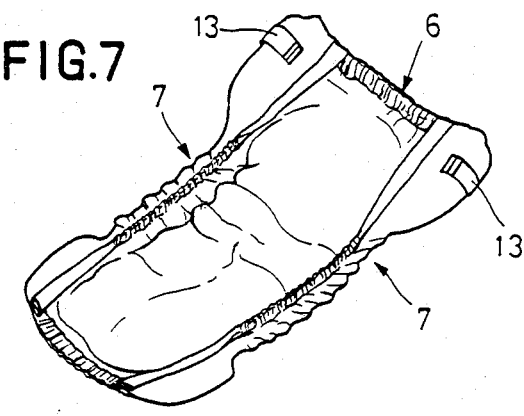
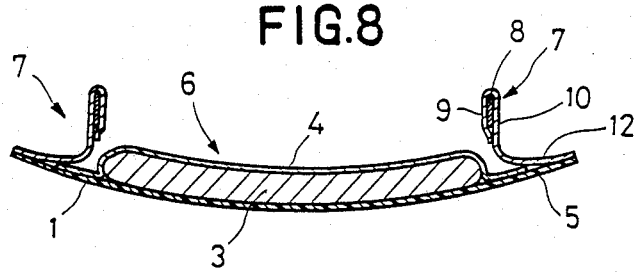

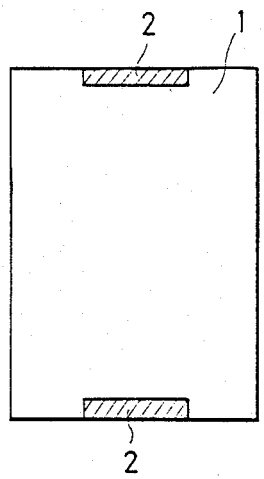 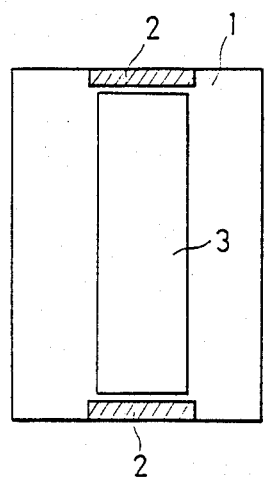 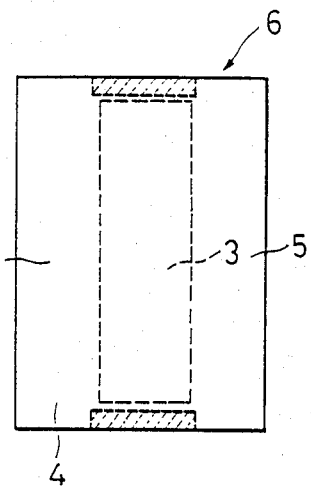
FIG.10   FIG.11   FIG.12
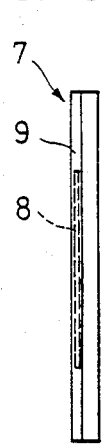 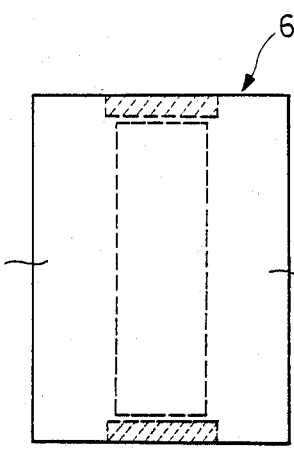 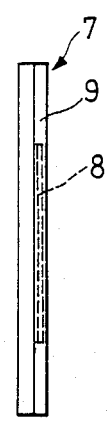
FIG.13A   FIG.13   FIG.13B

METHOD FOR MAKING WEARABLE ARTICLES

BACKGROUND OF THE INVENTION

The present invention relates to a method for making wearable articles such as disposable diapers, disposable diaper covers or the like and, more particularly, to a method for forming side flaps on opposite sides of such articles and for incorporating elastic members into these side flaps to provide a fitness around the wearer's legs.

It is well known, for example, in disposable diaper, to form the side flaps of high flexibility on the opposite sides thereof and to incorporate the elastic members into said side flaps to provide the desired fitness around the wearer's legs so that this disposable diaper may be assembled in the form of pants in actual use, and such disposable diaper is the one which has been most commonly used in practice.

The side flaps in such diaper of the prior art generally comprise the portions of the topsheet and the backsheet extending from opposite sides of the absorbent core which has top and bottom sides covered with said topsheet and said backsheet, respectively. In other words, the respective sheets thus forming together the side flaps are respectively continuous.

However, formation of the side flaps simply from the topsheet and the backsheet in the articles such as disposable diapers which must be mass-produced at a high rate from the economical viewpoint would be encountered by various problems as following.

(a) It is impossible to form the side flaps from material which is different from the topsheet and/or the backsheet, for example, material being superior in its air-permeability, to said backsheet so as to improve an effect for preventing the interior of the articles from being steamed;

(b) When it is desired to provide said side flaps with a specific structure so as to insure that the side flaps may come in close contact around the wearer's legs in actual use of the article and thereby perfectly block excretion, it is difficult in practice to realize such structure on the production line simultaneously of formation of main bodies of the individual articles. Even if it is possible to do so, such manner of operation is not suitable for the disposable articles which require a high speed mass-production from the economical viewpoint; and (c) Also when it is desired to vary factors such as the width of each side flap and the distance between the opposite elastic members selectively in the front area and the rear area of the article, the inconvenience similar to that as set forth in the precedent paragraph (b).

Accordingly, it is an essential object of this invention to provide an improved method for making wearable articles such as disposable diapers allowing the above-mentioned problems to be effectively solved by forming a part of the side flaps separately of the main body of each article and then joining this part to said main body on the production line.

SUMMARY OF THE INVENTION

The present invention proposes a method for making wearable articles such as disposable diaper comprising the steps of forming a main body of each article having first side flaps extending outwards from lateral opposite sides thereof, forming second side flaps separately of said main body, providing each of said second side flaps along its one side edge with an elastic member, and joining each of said second side flaps along the other side edge as well as longitudinally opposite ends thereof onto the top surface of the associated first side flap so that the one side edge of said second side flap containing therein said elastic member is directed outwards.

In accordance with the present invention, the main body of the article, on one side, and the second side flaps to be provided on the opposite sides thereof as complementary portions of the complete side flaps and incorporated with the associated elastic members, on the other side, are formed separately of each other and then the latters are overlapped upon the formers at the opposite sides thereof. In this manner, the problems as have previously been pointed out can be effectively solved. More specifically, when the entire side flaps are formed by the portions of the topsheet and/or the backsheet, the components of said main body, extending from the opposite sides of said main body, the side flaps thus formed will have, of course, the same air-permeable characteristic as said component of said main body. According to the present invention, the second side flaps are separately formed of material which is superior in its air-permeability, to said components of the main body and thereby an effect for preventing the interior of the article from being steamed or becoming stuffy is improved.

The second side flaps may be provided along portions of folding with the elastic members and longitudinally opposite ends of said folding portions may be fixed to selectively raise, collapse or incline these folded portions. The present invention allows such side flaps to be formed in a relatively easy manner.

Furthermore, a distance between the elastic members disposed in the article is preferably wider at least in the rear area than in the central (crotch) area of the article in order to improve a fitness of the article around the wearer's legs and this is achieved by proper area of the width and the angle over and at which the second side flaps are folded as well as the width and the angle over and at which the non-folded portions of the second side flaps are joined to the respective first side flaps of the main body of the article. The present invention allows also such side flaps to be formed in a relatively simple manner.

Accordingly, the present invention permits the side flaps of the rather specific structure as mentioned above to be incorporated into the article without any significant reduction of the desired productivity at a high rate.

BRIEF DESCRIPTION OF THE DRAWINGS

FIGS. 1 through 5 are plan views sequentially illustrating a process of forming disposable diaper as a first embodiment of this invention;

FIG. 6 is a plan view illustrated a completed diaper;

FIG. 7 is a perspective view of this completed diaper;

FIG. 8 is a cross-sectional view of the same;

FIGS. 10 through 14 are plan views sequentially illustrating a process of forming disposable diaper as a second embodiment of this invention;

PREFERRED EMBODIMENTS

Figure 9:
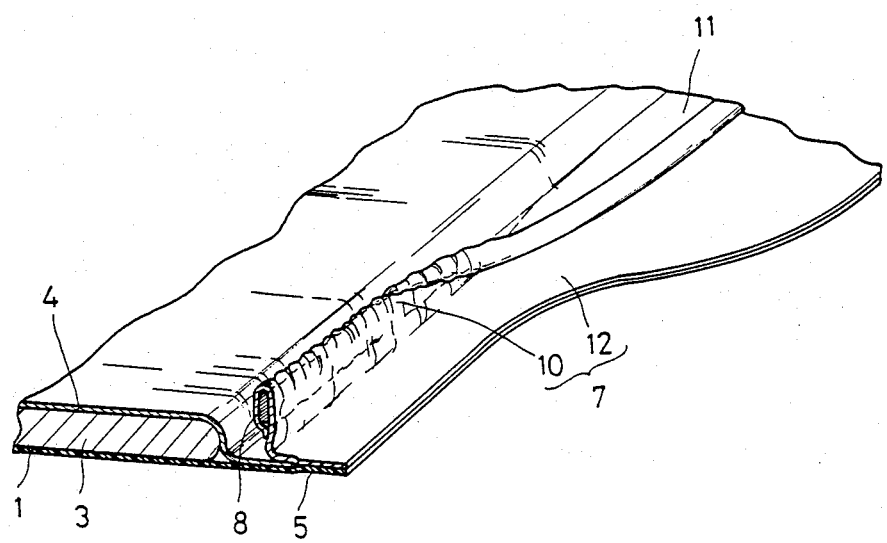
FIG. 9 is a partial perspective view illustrating a portion of said completed diaper including a side flap.

The present invention will be described by way of disposable diapers as preferred embodiments in reference with the accompanying drawings.

FIGS. 1 through 9 illustrate the first embodiment of the present invention.

Referring to FIGS. 1 through 3, longitudinally opposite edges of a water-impermeable backsheet 1 are centrally provided on top surface with elastic members 2 adopted to provide a desired fitness around the wearer's waist preferably by means of adhesive, an absorbent core 3 is fixed to the top surface of the backsheet 1 preferably by means of adhesive in an area defined between said opposite elastic members 2, and then said elastic members 2 and said core 3 are covered with a water-permeable topsheet 4 slightly larger than said core 3 preferably by means of adhesive. Thus, a main body 6 of the diaper is formed, which has first side flaps 5 extending from opposite side edges of the core 3 outwardly.

Now referring to FIG. 4, second side flaps 7 are formed separately of the main body 6 from a water-impermeable sheet considerably narrower than the backsheet 1. Each of these second side flaps 7 is provided along one side edge with an elastic member 8 for a fitness around each leg of the wearer preferably by means of adhesive and this side edge 9 is folded to cover said elastic member (FIG. 4A). After the flap 7 has been reversed, the edge portion containing the elastic member 8 is folded outwards (FIG. 4B) and this folded portion 10 is joined at its longitudinally opposite ends 11 on the top surface of the non-folded portion 12 (FIGS. 7 and 9). The second side flap 7 is further provided on its side opposite to said side edge along which the elastic member 8 extends adjacent one of longitudinally opposite ends with a tape fastener 13 for a fitness around the waist of the wearer preferably by means of adhesive before or after folding of said portion 10. Formation of the second side flap 7 is thus completed.

Referring to FIGS. 5 and 6, the second side flaps 7 are joined over the non-folded areas 12 with their bottom surfaces facing downwards onto the respective first side flaps 5 of the main body 6 preferably by means of adhesive so that the respective elastic members 8 are on inner sides (FIGS. 7 and 9). Such joining occurs along lines as indicated by chain lines 14 (FIG. 5) but the bonding may extend outside these chain lines into areas 15 (FIG. 5). Thereafter the areas 15 of both first and second side flaps 5 and 7 may be cut to provide a contour which enables a desired fit against the wearer's body to be achieved (FIG. 6).

Said folding of the portions 10, said joining of the longitudinally opposite ends thereof and said provision of the tape fasteners 13 may be performed during or after joining of the second side flaps 7 to the main body 6.

FIGS. 10 through 18 illustrate a second embodiment of the present invention.

Referring to FIGS. 10 through 12, longitudinally opposite edges of a water-impermeable backsheet 1 are centrally provided on the top surface with elastic members 2 for a fitness around the wearer's waist preferably by means of adhesive, an absorbent core 3 is fixed to the top surface of the backsheet 1 preferably by means of adhesive in an area defined between said opposite elastic members 2, and then said elastic members 2 and said core 3 are covered with a water-permeable topsheet 4 having the same dimensions as said backsheet 1 preferably by means of adhesive. Thus, a main body 6 of the diaper is formed, which has first side flaps 5 extending outwards from opposite side edges of the core 3.

As seen in FIG. 13, second side flaps 7 are formed separately of the main body 6 from a water-impermeable sheet considerably narrower than the backsheet 1. Each of these second side flaps 7 is provided along one side edge with an elastic member for a fitness around each of the wearer's legs preferably by means of adhesive and this edge 9 is folded to cover said elastic member. Formation of the second side flaps 7 is thus completed.

Figure 14:
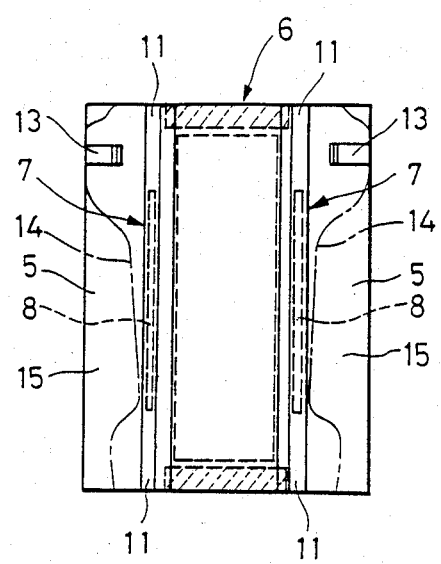
Figure 15:
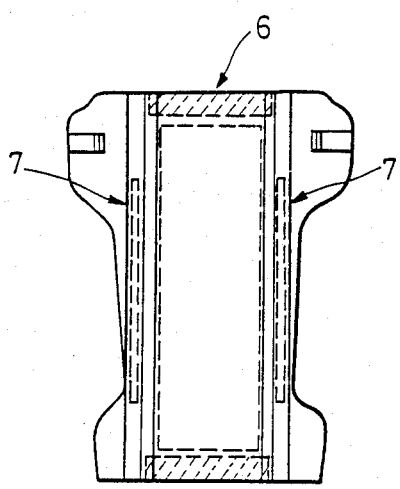
FIG. 15 is a plan view illustrating a completed diaper.
Figure 16:
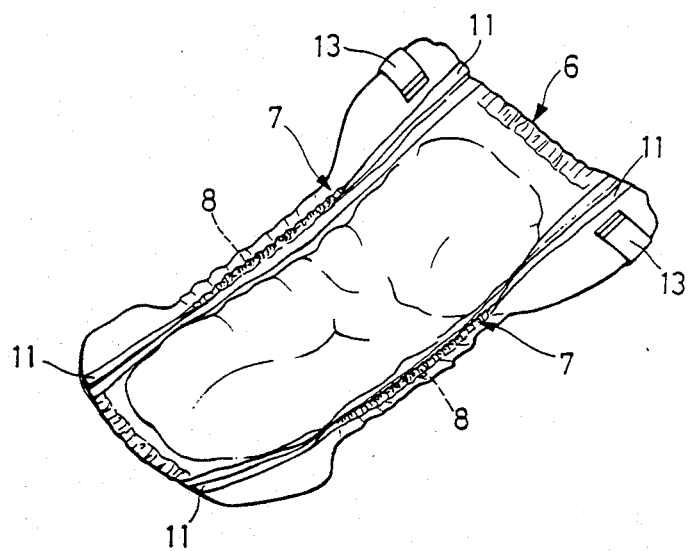
FIG. 16 is a perspective view of the same.
Figure 17:
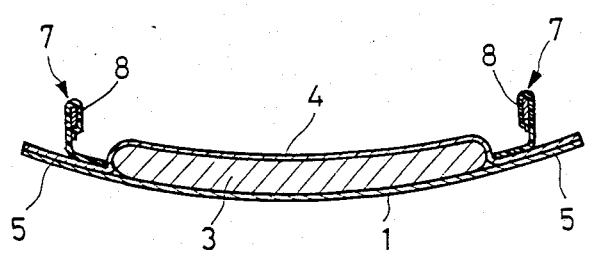
FIG. 17 is a cross-sectional view of the same.
Figure 18:
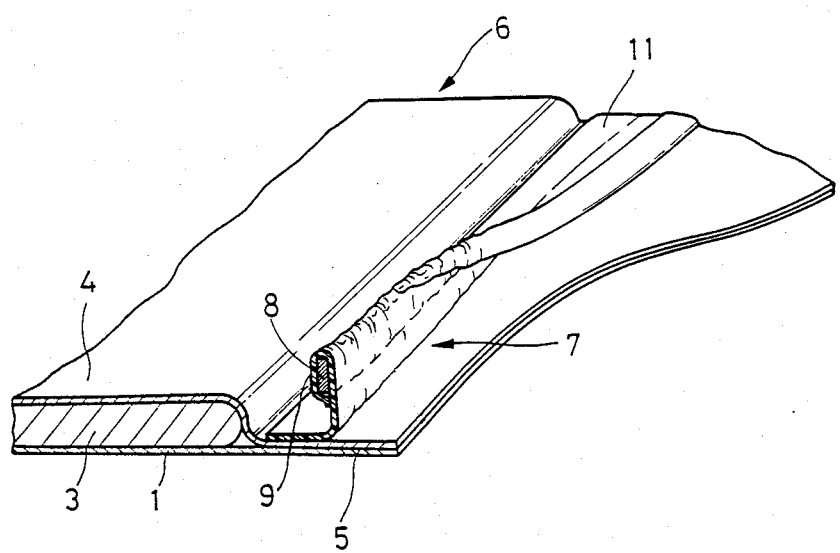
FIG. 18 is a partial perspective view illustrating a portion of this completed diaper including a side flap.

Referring to FIGS. 14 and 15, each of the second side flaps 7 so oriented that the side edge containing the associated elastic member 8 is directed outwards is joined along the inner side edge and the longitudinally opposite ends 11 of said side edge containing said associated elastic member 8, with the bottom surfaces of these components facing downwards, onto the top surface of the corresponding first side flap 5 of the main body 6 preferably by means of adhesive (FIGS. 16 through 18). Thereafter, the outer areas 15 extending outside lines 14, respectively, are cut off along these lines 14, respectively, so that the first side flaps 5 may be configured to provide a desired fitness against the wearer's body.

Each of the first side flaps 5 is provided adjacent one of its longitudinally opposite ends with a tape fastener 13 so that this tape fastener 13 is laterally opposite to the corresponding tape fastener 13 provided on the other of the first side flaps. With an arrangement in which the opposite side edges of the first side flaps 5 coincide with the opposite side edges of the second side flaps 7, said tape fasteners 13 will be provided on both the first side flaps and the second side flaps.

The backsheet 1 may be of material such as air-permeable plastic or laminate sheet of said film and non-woven fabric, the elastic members 2, 8 may be of material such as polyurethane foam or rubber, the topsheet 4 may be of material such as non-woven fabric or porous plastic film and the second side flaps may be of material such as air-permeable plastic film, laminate sheet of said film and non-woven fabric or non woven fabric treated with suitable repellent.

When the second side flaps 7 are made of material such as water-proof non-woven fabric or laminate sheet of plastic film and non-woven fabric and these flaps have touches being different depending on their top and bottom sides, the component providing an agreeable touch, for example, non-woven fabric may be adapted to be in direct contact with the wearer's skin.

While the embodiments have been illustrated as having the second side flaps 7 on the opposite sides of the diaper being joined to the main body so as to be spaced from each other uniformly throughout the front, crotch and rear areas of the diaper, it is also possible within the scope of the invention to join said both second side flaps 7 to the main body so that said spacing is gradually enlarged from that in the front area to that in the rear area. In this way, the spacing of the elastic members 8 disposed on the opposite sides of the diaper also is gradually enlarged from that in the front area to that in the rear area and this allows the elastic members 8 to have a mutual spacing necessary to provide a proper fitness against the wearer's hip which is wider than both the crotch area and the belly area.

Although it is not essential for this invention to provide the diaper with the elastic member 2 for the waist, it will be convenient to dispose these elastic members 2 along the longitudinally opposite edges of the backsheet 1 and the topsheet 4, if they are provided. In view of the typical process of making the diaper in which the backsheet 1 and the topsheet 4 are continuously fed in the direction of production line and the continuous web of diapers are cut into the individual diapers upon completion, said elastic members 2 for the waist each having a width twice the final width of the individual elastic members are disposed so that their longitudinally central lines come just on the cutting lines. In this manner, the respective elastic members having said double width are divided into two parts of equal width as the web of diapers is cut into the individual diapers wherein one half of said double width elastic member is distributed to the precedent diaper while the other half is distributed to the following diaper. Accordingly, an efficiency for provision of said elastic members is significantly improved.

The opposite sides of the topsheet 4 may be enfolded between the bottom surface of the core 3 and the backsheet 1 along the opposite sides of said core 3, when it is necessary or considered to be more convenient.

In the diaper thus formed, the second side flaps 7 are raised except their longitudinally opposite ends 11 when the respective elastic members 8 are in contracted condition, as seen in FIGS. 7 through 9 and FIGS. 16 through 18. However, when the elastic members 8 are in sufficiently extended condition as shown by FIGS. 6 and 15 as a result of the diaper being longitudinally tensioned, the second side flaps 7 collapse outwards. Therefore, the second side flaps are inclined at a certain angle outwardly but without being perfectly collapsed so far as the elastic members 8 are in a moderately extended condition. It is due to the specific arrangement that the outer side edges containing the associated elastic members 8 are directed outwards and fixed at the longitudinally opposite ends thereof that the second side flaps 7 may be raised, collapsed or inclined depending on a degree at which the elastic members 8 are extended. Such function of the second side flaps 7 is very effective to fit these side flaps closely around the wearer's legs, to maintain reliable engagement thereof around the wearer's legs even when the wearer moves the legs freely and thereby to prevent excretion leakage from occurring around the wearer's legs.

What is claimed is:

1. A method of making wearable absorbent articles which comprises the steps of
    (a) forming a main body (6) comprising an elongated absorbent core (3) mounted between a topsheet (4) and a backsheet (3), said topsheet (4) and said backsheet (3) being joined together so as to extend laterally outwardly from the sides of said absorbent core (3) to form first side flaps (5) on each lateral side of said absorbent core (3),
    (b) providing second side flaps by
        (1) forming elongated strips (7) of water-impervious material that have an upper surface and a lower surface,
        (2) folding over on itself a portion (10) of each elongated strip (7) adjacent a longitudinal edge thereof and incorporating in said folded over position (10) an elongated elastic member (8), leaving a not-folded portion (12) in each side flap (7),
        (3) rotating said folded portion (10) through an angle of about 180° with respect to said unfolded portion (12), and
        (4) joining longitudinally opposite ends of said folded over portions (10) to the top surface of the adjacent non-folded portion (12), and
    (c) joining the bottom surface of the non-folded portion of said second side flaps (7) to the upper surface of said first side flaps (5) so that a portion of the folded portions (10) extend vertically upwards from the topsheet portion (4) of said side flaps (5) and the remainder of said folded portions extend in a direction away from said absorbent core (3).

2. A method according to claim 1 wherein said articles are disposable diapers.

3. A method according to claim 1 wherein said articles are disposable diaper covers.

* * * * *